United States Patent
Foster et al.

(10) Patent No.: US 11,235,145 B2
(45) Date of Patent: Feb. 1, 2022

(54) DIRECTIONAL SUBCUTANEOUS IMPLANTABLE CARDIOVERTER DEFIBRILLATOR ELECTRODE

(71) Applicant: CARDIAC PACEMAKERS, INC., St. Paul, MN (US)

(72) Inventors: Arthur J. Foster, Blaine, MN (US); G. Shantanu Reddy, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 380 days.

(21) Appl. No.: 15/804,206

(22) Filed: Nov. 6, 2017

(65) Prior Publication Data
US 2018/0133458 A1    May 17, 2018

Related U.S. Application Data

(60) Provisional application No. 62/423,521, filed on Nov. 17, 2016.

(51) Int. Cl.
*A61N 1/05* (2006.01)
*A61N 1/39* (2006.01)

(52) U.S. Cl.
CPC ............. *A61N 1/0504* (2013.01); *A61N 1/05* (2013.01); *A61N 1/3956* (2013.01)

(58) Field of Classification Search
CPC ....... A61N 1/0504; A61N 1/05; A61N 1/3956
See application file for complete search history.

(56) References Cited

U.S. PATENT DOCUMENTS

| | | | |
|---|---|---|---|
| 4,291,707 | A | 9/1981 | Heilman et al. |
| 5,203,348 | A | 4/1993 | Dahl et al. |
| 5,331,966 | A | 7/1994 | Bennett et al. |
| 5,477,855 | A | 12/1995 | Schindler et al. |
| 5,534,022 | A | 7/1996 | Hoffmann et al. |
| 5,865,728 | A | 2/1999 | Moll et al. |
| 6,038,483 | A | 3/2000 | Kenknight et al. |
| 6,148,230 | A | 11/2000 | Kenknight |
| 6,330,481 | B1 | 12/2001 | Van Wijk et al. |
| 6,647,292 | B1 | 11/2003 | Bardy et al. |
| 6,721,597 | B1 | 4/2004 | Bardy et al. |
| 7,070,576 | B2 | 7/2006 | O'Brien et al. |
| 7,149,575 | B2 | 12/2006 | Ostroff et al. |
| 7,288,096 | B2 | 10/2007 | Chin |

(Continued)

FOREIGN PATENT DOCUMENTS

WO          0241946 A2     5/2002

OTHER PUBLICATIONS

International Search Report and Written Opinion dated Feb. 13, 2018 for International Application No. PCT/US2017/060140.

(Continued)

*Primary Examiner* — Joseph M Dietrich
(74) *Attorney, Agent, or Firm* — Seager, Tufte & Wickhem LLP

(57) ABSTRACT

Implantable device systems include an electrical lead with one or more electrodes and a shield. The shield is attached to the electrical lead with the shield covering a first side of the electrode and extending laterally away from the electrode. The shield directs energy from at least one of the electrodes of the the electrical lead in a direction away from the shield.

18 Claims, 11 Drawing Sheets

(56) References Cited

U.S. PATENT DOCUMENTS

| | | |
|---|---|---|
| 7,299,092 B2 | 11/2007 | Bardy et al. |
| 7,499,758 B2 | 3/2009 | Cates et al. |
| 7,522,959 B2 | 4/2009 | Hauser et al. |
| 7,570,997 B2 | 8/2009 | Lovett et al. |
| 7,632,288 B2 | 12/2009 | Wu |
| 7,657,322 B2 | 2/2010 | Bardy et al. |
| 7,684,864 B2 | 3/2010 | Olson et al. |
| 7,734,343 B2 | 6/2010 | Ransbury et al. |
| 7,758,604 B2 | 7/2010 | Wu et al. |
| 7,769,472 B2 | 8/2010 | Gerber |
| 7,890,191 B2 | 2/2011 | Rutten et al. |
| 7,976,557 B2 | 7/2011 | Kunis |
| 8,050,774 B2 | 11/2011 | Kveen et al. |
| 8,079,959 B2 | 12/2011 | Sanghera et al. |
| 8,157,813 B2 | 4/2012 | Ko et al. |
| 8,231,637 B2 | 7/2012 | Greenberg et al. |
| 8,241,210 B2 | 8/2012 | Lunsford et al. |
| 8,285,375 B2 | 10/2012 | Bardy et al. |
| 8,364,280 B2 | 1/2013 | Marnfeldt et al. |
| 8,483,841 B2 | 7/2013 | Sanghera et al. |
| 8,491,615 B2 | 7/2013 | Manderfeld et al. |
| 8,577,454 B2 | 11/2013 | Bardy et al. |
| 8,644,926 B2 | 2/2014 | Ostroff et al. |
| 8,660,668 B2 | 2/2014 | Bardy et al. |
| 8,706,217 B2 | 4/2014 | Bardy et al. |
| 8,718,760 B2 | 5/2014 | Bardy et al. |
| 8,718,793 B2 | 5/2014 | O'Connor |
| 8,801,729 B2 | 8/2014 | Ko et al. |
| 8,986,335 B2 | 3/2015 | Chin |
| 9,079,035 B2 | 7/2015 | Sanghera et al. |
| 9,216,284 B2 | 12/2015 | O'Connor |
| 2004/0215308 A1 | 10/2004 | Bardy et al. |
| 2012/0029335 A1 | 2/2012 | Sudam et al. |
| 2012/0035616 A1* | 2/2012 | Olsen .................. A61N 1/3718 606/129 |
| 2014/0330326 A1 | 11/2014 | Thompson-Nauman et al. |
| 2016/0213270 A1 | 7/2016 | Cao et al. |
| 2016/0310746 A1 | 10/2016 | Greenhut et al. |
| 2017/0020551 A1 | 1/2017 | Reddy et al. |
| 2017/0021159 A1 | 1/2017 | Reddy et al. |

OTHER PUBLICATIONS

A Patient's Guide-Living with your S-ICD System, 2012.
Ferrari et al., Journal of Arrhythmia, 1-3, 2015.
Lieberman et al., MDT Anterior Posterior SubQ Testing Article, Heart Rhythm, vol. 5, No. 1, 28-34, 2008.
Jolley et al., Finite element modeling of subcutaneous implantable defibrillator electrodes in an adult torso, Heart Rhythm (2009).
Weiss et al., Arrhythmia/Electrophysiology, Circulation, 128, 944-954, 2013.

* cited by examiner

DIRECTIONAL SUBCUTANEOUS IMPLANTABLE CARDIOVERTER DEFIBRILLATOR ELECTRODE

CROSS REFERENCE TO RELATED APPLICATIONS

The present application claims the benefit of and priority to U.S. Provisional Patent Application Ser. No. 62/423,521, filed on Nov. 17, 2016, titled DIRECTIONAL SUBCUTANEOUS IMPLANTABLE CARDIOVERTER DEFIBRILLATOR ELECTRODE, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

The first approved commercial version of the S-ICD System™ delivered approximately 80 Joules of energy for defibrillation therapy. To supply this amount of energy in a timely fashion over the life of the device, three high power capacitors and three batteries were used in the first approved S-ICD System™ devices. Enhancements to reduce the total energy required may allow for reduction in size by facilitating the use of smaller or fewer batteries and/or capacitors. In addition, it is desired to increase the already high likelihood of successful implantation as measured by the ability to convert induced ventricular fibrillation at implant using 65 Joule therapy (an imputed success rate of 96.5% was calculated in PMA P11042: FDA Summary of Safety and Effectiveness Data, available online at http://www.accessdata.fda.gov/cdrh_docs/pdf11/P110042b.pdf). New and alternative defibrillation lead and electrode designs, as well as alternative implant tools and methods, may be useful to achieve these goals.

OVERVIEW

The present inventors have recognized, among other things, that a problem to be solved is the provision of new and different lead designs for implantable defibrillators. Various new electrode designs are described below. Some example designs include a shield attached to an electrical lead, where the shield may cover a first side of an electrode on the lead. The shield may have wings that extend laterally away from the electrode and may direct energy from the electrode in a direction away from the shield. Some examples take the form of methods of using such electrodes.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
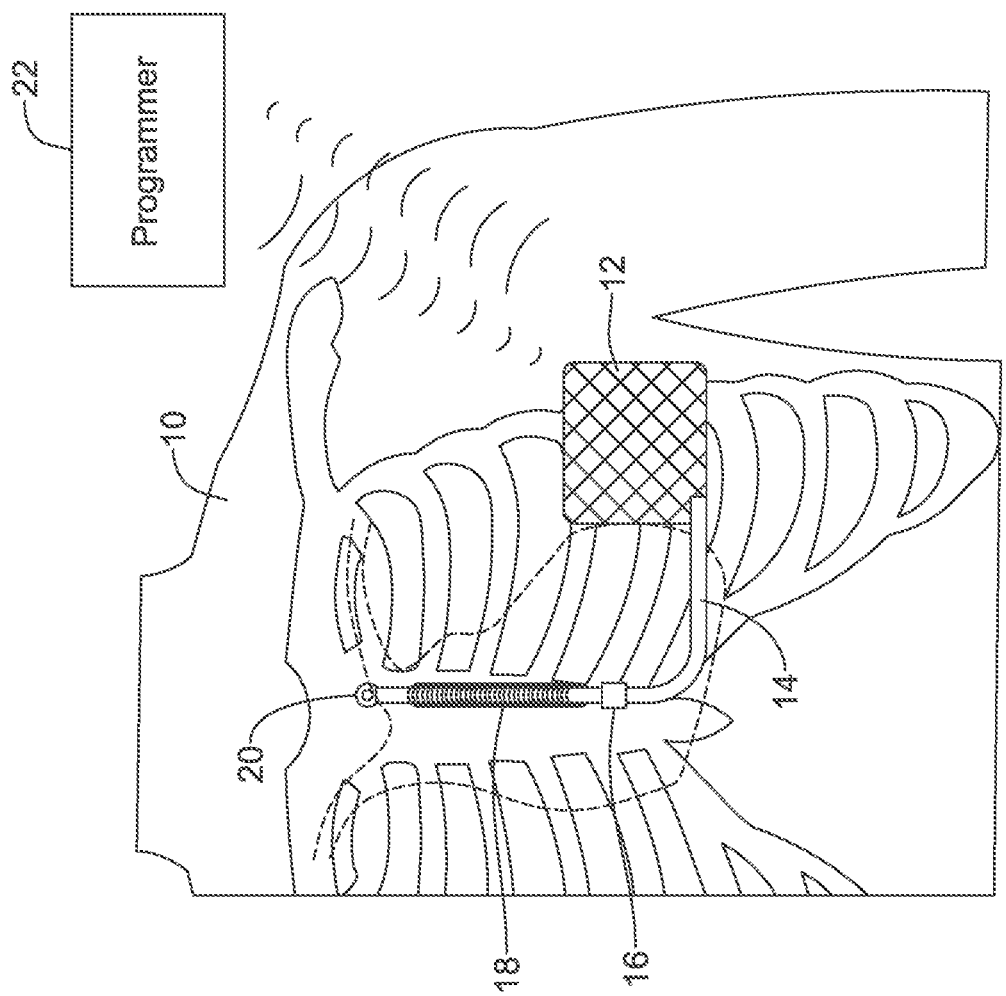
FIG. 1 shows an illustrative implantable cardiac rhythm management system.

FIG. 1 shows a subcutaneous implantable cardioverter-defibrillator (S-ICD) System™ from Cameron Health, Inc., and Boston Scientific Corporation, as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may include componentry appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12. Though not shown, the system may also be used with a remote monitor, as such systems are known in the art.

The placement of a defibrillator system entirely subcutaneously can be associated with a need for higher voltage, power and/or current when delivering therapy defibrillation and/or pacing therapy. One effect of higher power and/or voltage requirements is that the size of the implantable canister 12 may be limited by a need, for example, to include two or even three batteries and/or high power capacitors. For example, the S-ICD System® as approved by the United States Food and Drug Administration in 2012 had three batteries and three high power capacitors, which consumed the vast majority of the implantable device volume.

One proposed solution for reduction of power is placement of the lead 14 beneath the sternum, such as discussed in Guenther et al., Substernal Lead Implantation: A Novel Option to Manage DFT Failure in S-ICD Patients, Clin. Res. Cardiol (2015) 104:189-191. Some tools and methods to perform substernal implantation are discussed in US Patent Application Pub. No. 20170021159, titled SUBSTERNAL PLACEMENT OF A PACING AND/OR DEFIBRILLATING ELECTRODE, the disclosure of which is incorporated herein by reference.

The enhancements suggested in the present patent application may be implemented in subcutaneous-only, substernal, and/or other lead systems. An example of an "other" lead system may include a system configured for implantation within one or both of the internal thoracic vein (ITV), also known as the internal mammary vein, as in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

It should be noted that while the example of FIG. 1 shows a device implanted without any leads and/or electrodes in or on the heart, the enhancements herein may also be used in systems that include one or more such leads or electrodes. Additionally, while FIG. 1 shows a left lateral or axillary canister 12 with a parasternal lead 14, other positions may be used instead such as those shown in U.S. Pat. Nos. 6,721,597 and 7,149,575, the disclosure of which are incorporated herein by reference. For example, and without limitation, the canister 12 may be placed anterior, right-sided, posterior, abdominal, pectoral/infraclavicular, or placed in any other desired position, with the lead 14 extending vertically or horizontally on the anterior, side, or posterior of the patient's torso, for example. Additional enhancements are desired, both in terms of the electrode and lead to be implanted as well as methods and tools for such implantation.

Figure 2:
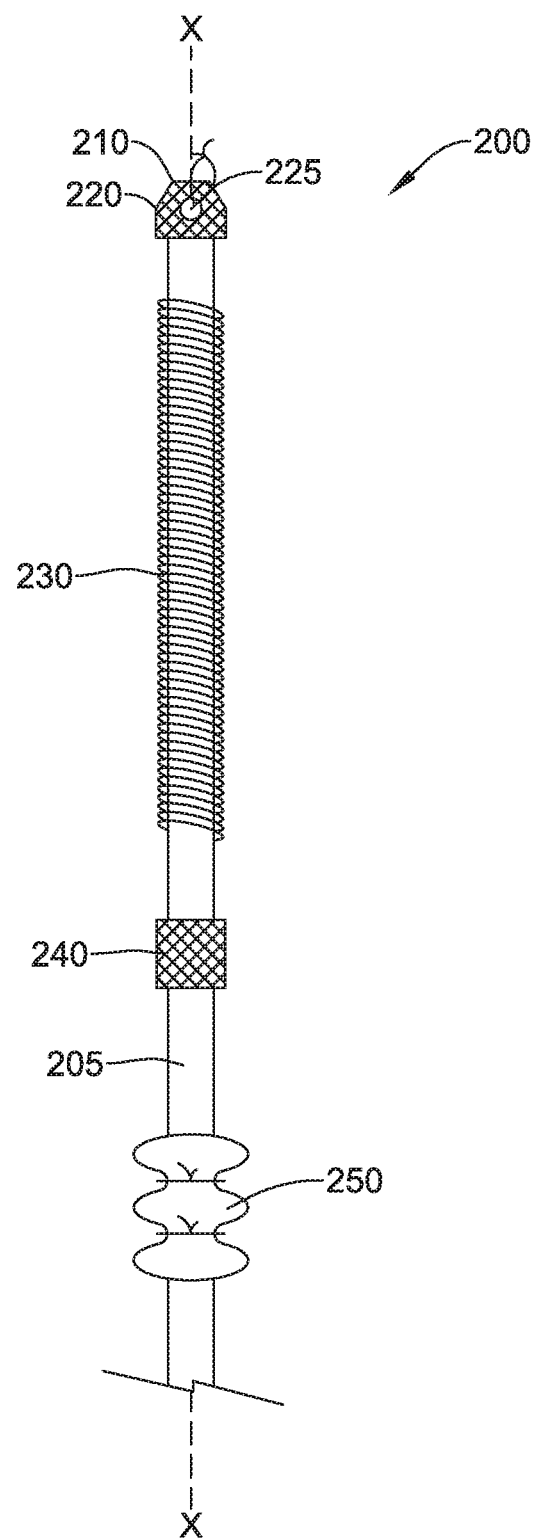
FIG. 2 shows an electrical lead for use with an implantable cardiac rhythm management system.

FIG. 2 shows an illustrative distal portion of a subcutaneous lead. The subcutaneous lead 200 is shown including a lead body 205, a distal tip electrode 220 disposed at the distal end 210 of the lead body 205, a coil electrode 230 and a proximal electrode 240. An attachment feature is shown at the distal tip electrode 220 as a suture hole 225. A suture sleeve 250 is shown proximal of the proximal electrode 240. The suture hole 225 and suture sleeve 250 can be used to suture the lead into position in the subcutaneous tissue of a patient, providing anchoring of the lead 200.

Lead 200 is shown for illustrative purposes, however, other designs and configurations including fewer, more or different electrodes 240, 230, 220, or contacts, may be used. Additional design elements such as bifurcation or other splitting, or other designs may be used instead with an anchoring device attached at the time of implant. The lead 200 is not shown as including a passageway for a stylet to use during introduction, however, a lumen for that purpose may be provided if desired. In the illustrative example, the lead 200 may have a body that contains passageways having connectors therein for coupling the proximal contacts to the coil electrode 230, proximal electrode 240, and/or distal electrode 220. The distal tip electrode 220 is shown with a suture hole 225. Other designs may be used. In some embodiments, a suture hole 225, or other fixation means, may not be required and/or may not be provided.

As used herein, a coil electrode 230 may be a helically wound filament or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

The shocking coil electrode 230 may have a round or generally flattened cross-sectional configuration. Other cross-sectional shapes may also be used, including, but not limited to, rectangular, polygonal, circular, square, etc. The coil electrode 230 may have a length that is generally larger than a diameter. The length of the coil electrode 230 may be in the range of 40 to 110 millimeters (mm), 60 to 100 mm, 70 to 90 mm or about 80 mm. The diameter of the electrode 230 may be in the range of 0.5 mm to 6 mm, 1 mm to 5 mm, 2 mm to 4 mm, or about 3 mm.

The coil electrode 230 may be formed as a subassembly and placed over the lead body 205. Alternatively, the coil electrode 230 may be formed as a unitary structure with or otherwise formed over the lead body 205. While not explicitly shown, the coil electrode 230 may include a lumen or passageway for receiving a stylet or other delivery aid. In some instances, adjacent windings of the coil electrode 230 may be in contact with one another while in other instances adjacent windings may be spread out or spaced a distance from one another, as desired.

The positioning and/or spacing of the electrodes 240, 230, 220 may be adjusted and/or reconfigured to optimize sensing and/or therapy delivery. Some examples of such spacing are discussed in U.S. Pat. No. 8,483,841 ELECTRODE SPACING IN A SUBCUTANEOUS IMPLANTABLE CARDIAC STIMULUS DEVICE, the disclosure of which is incorporated herein by reference. For example, both sensing electrodes 240, 220 may be placed proximal to or distal to the coil electrode 230. It is contemplated that the electrodes 240, 230, 220 may be placed beneath the skin and over the ribcage of the patient. In other embodiments, the electrodes 240, 230, 220 may be placed in a sub sternal location using an implant procedure that may include a xiphoid or sub-xiphoid incision that allows for tunneling along the back side of the sternum. In further examples, the electrodes 240, 230, 220 may be placed in a parasternal location such as within one or both of the internal thoracic veins or arteries. The electrodes 240, 230, 220 may also be placed elsewhere as desired including for example, for use with right sided, anterior-posterior, or other implant positions.

The coil electrode 230 is illustrated in FIG. 2 as a single coil electrode. In other examples, a plurality of individual coil electrodes may be provided. For example, the coil electrode 230 may including any number of individual coil electrodes desired, such as, but not limited to, one, two, three, four, five, or more. Further, when a plurality of coil electrodes are provided, they may be positioned close to one another (e.g. touching) or spaced a distance, as desired.

A shield 320 as shown in FIGS. 3-9 may provide a larger surface area and/or shadow than a typical shocking coil electrode 230 alone. It is contemplated that increasing the surface area and/or shadow of the electrode assembly 300 may allow the defibrillation threshold to be lowered which may allow the canister, such as canister 12, to have a smaller profile. In some examples, a conductive surface may be provided on the shield 320 by providing copper, titanium, stainless steel or other conducive material on the shield surface on a portion that faces the direction of the cavity 330, effectively increasing the surface area of the lead but in a preferential direction. For such examples, attachment to a lead itself may be achieved using a conductive adhesive, for example. In other examples, no such increase in surface area is generated and instead the shield is generally non-conductive to block current flow therethrough.

Figure 3:
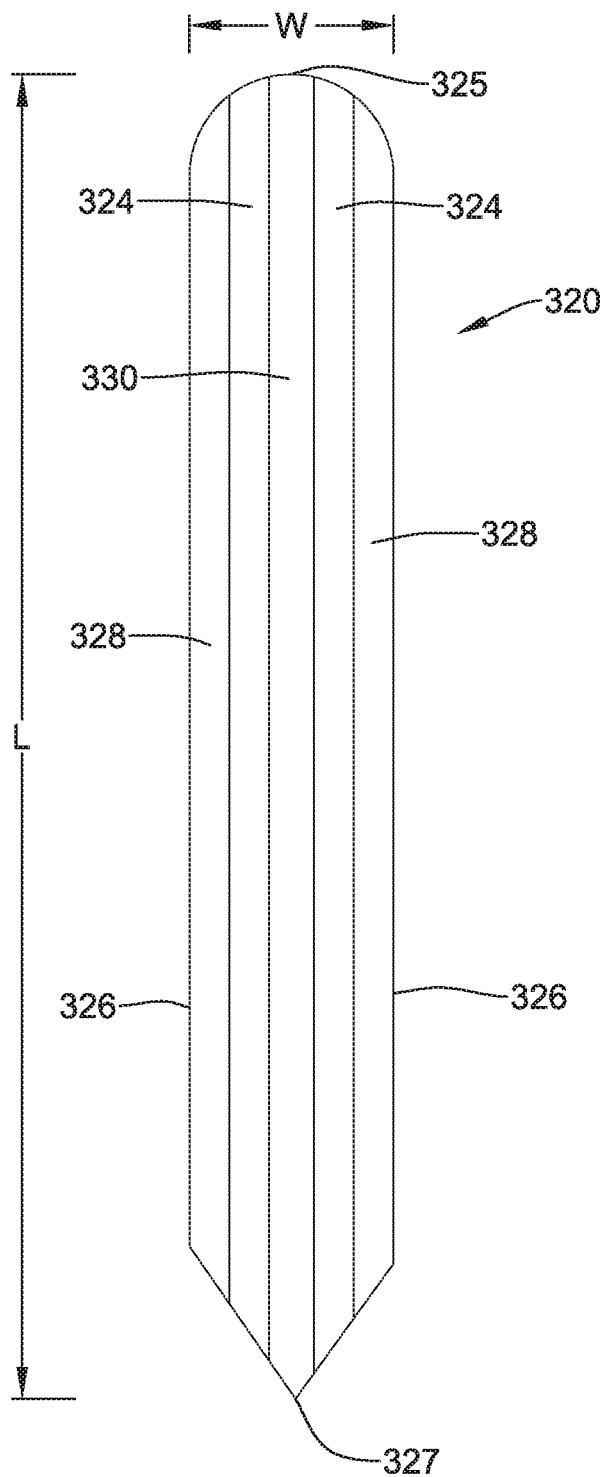
FIG. 3 shows a bottom view of a shield for use with an electrical lead.

FIG. 3 shows the shield 320 viewed from the bottom surface 324. The shield 320 may have a rounded distal end 325 and a pointed proximal end 327. In other embodiments, the proximal and distal ends may both be rounded, pointed, or have any other geometric shape. The shield 320 has a length L and a width W. In some examples, the shield 320 may have a length L of about 1 cm to about 16 cm. In other examples the shield 320 may have a length L of about 4 cm to about 10 cm. In still other examples the shield has a length of about 8 cm. The shield may be sized to adapt to a given electrode or lead by having a length equal to or up to 4 cm longer than the electrode. In some examples the shield 320 may have a width W in the range of about 6-20 mm. In other examples, for ease of implantation the shield 320 may have a width in the range of about 6 mm to about 12 mm. In some examples the shield 320 may be sized to cover the coil or coils on a lead with, for example, in the range of about zero to about 10 mm of shield extending beyond the proximal and/or distal end of the coil. In another example, there is 5 mm of shield extending beyond the proximal or distal end of the coil.

Figure 4:
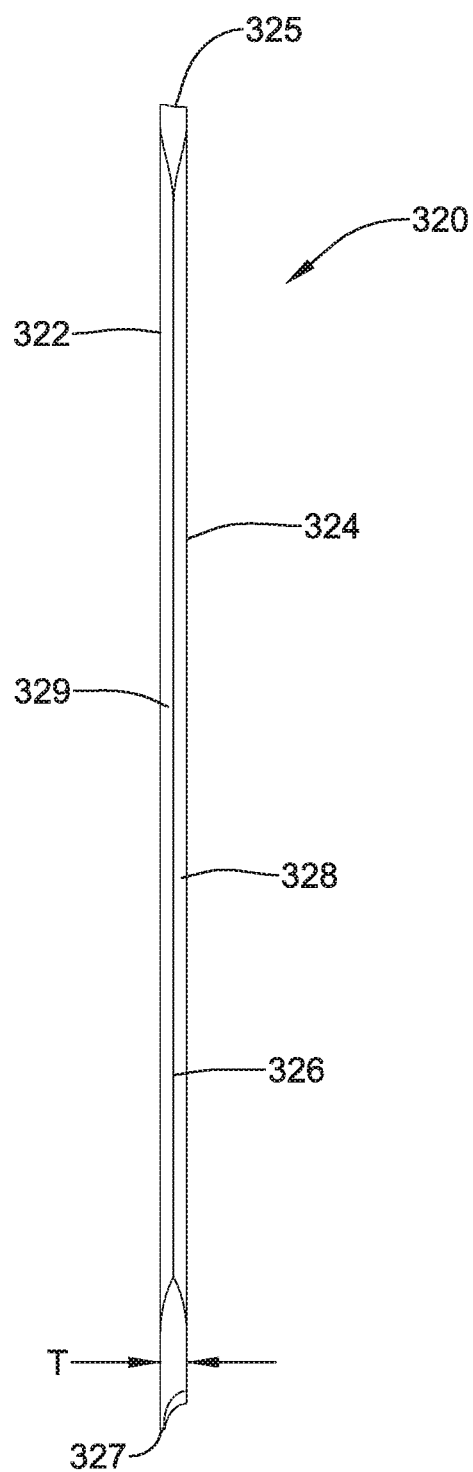
FIG. 4 shows a side view of the shield of FIG. 3.
Figure 5:
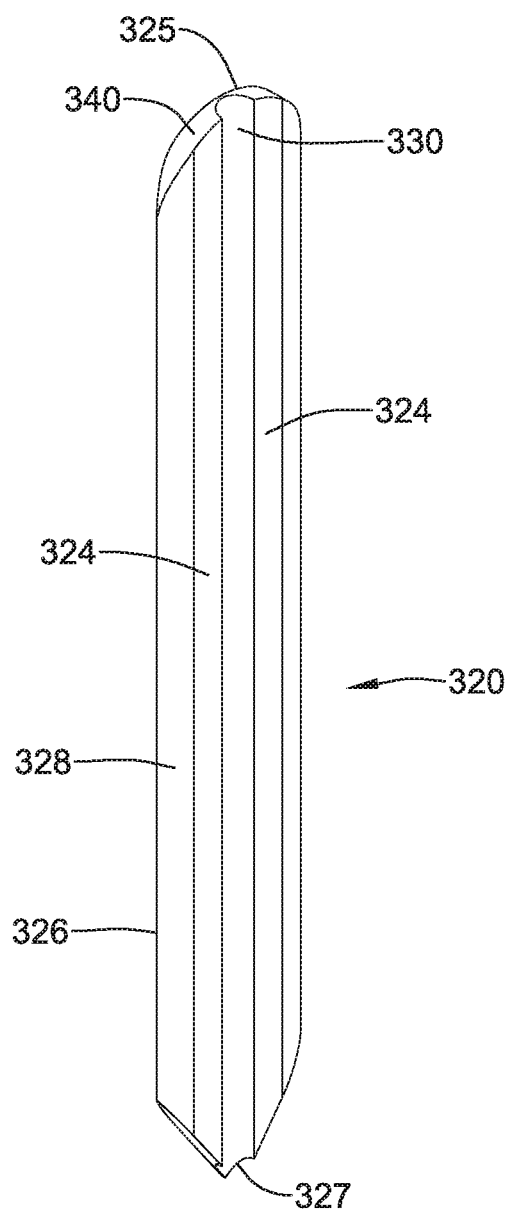
FIG. 5 shows a bottom perspective view of the shield of FIG. 3.

As shown in FIG. 4, the shield 320 may have a thickness T that is substantially less than the length L and width W. For example, the shield 320 may have a thickness T only slightly larger than a diameter D of the lead 200 in the region covered by the shield. In some examples, the shield 320 may have a thickness T in the range of about 1-3 mm. These ranges are illustrative and other sizes or ranges may be used in other embodiments in keeping with the spirit of the invention. The shield 320 may be hollow, having a space 340 extending between the top surface 322 and the bottom surface 324 and extending between the proximal end 327 and the distal end 325, as shown in FIG. 5. In other examples, the shield 320 may be a solid element.

In some examples, the shield 320 may have one or more attachment feature(s) such as a suture hole (not shown). The attachment feature may be positioned at any desired location along the shield. One such location may be at the distal end 325. In other examples, the shield 320 may be made of a material and have a thickness configured to allow a user to pass a suture directly through the shield. In such an example, the user may place one or more suture(s) at any desired location(s) as needed.

Figure 6:
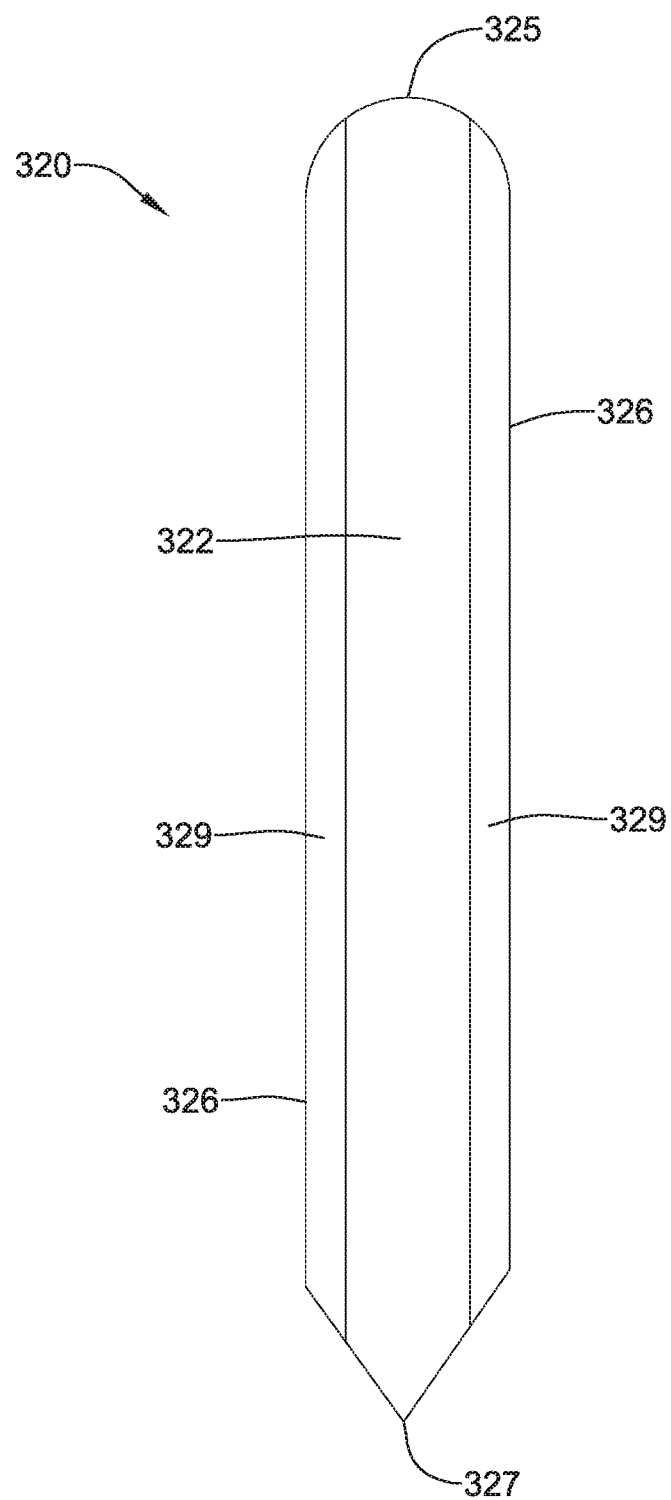
FIG. 6 shows a top view of the shield of FIG. 3.

FIG. 3 shows the different planes of the bottom of the shield 320, including the bottom surface 324, the bottom curved edge regions 328, and a cavity 330 to receive the lead. The top of the shield 320, as shown in FIG. 6, may include only the top surface 322 and the top curved end regions 329. The cavity 330 does not extend through the top surface 322 of the shield.

Figure 7:
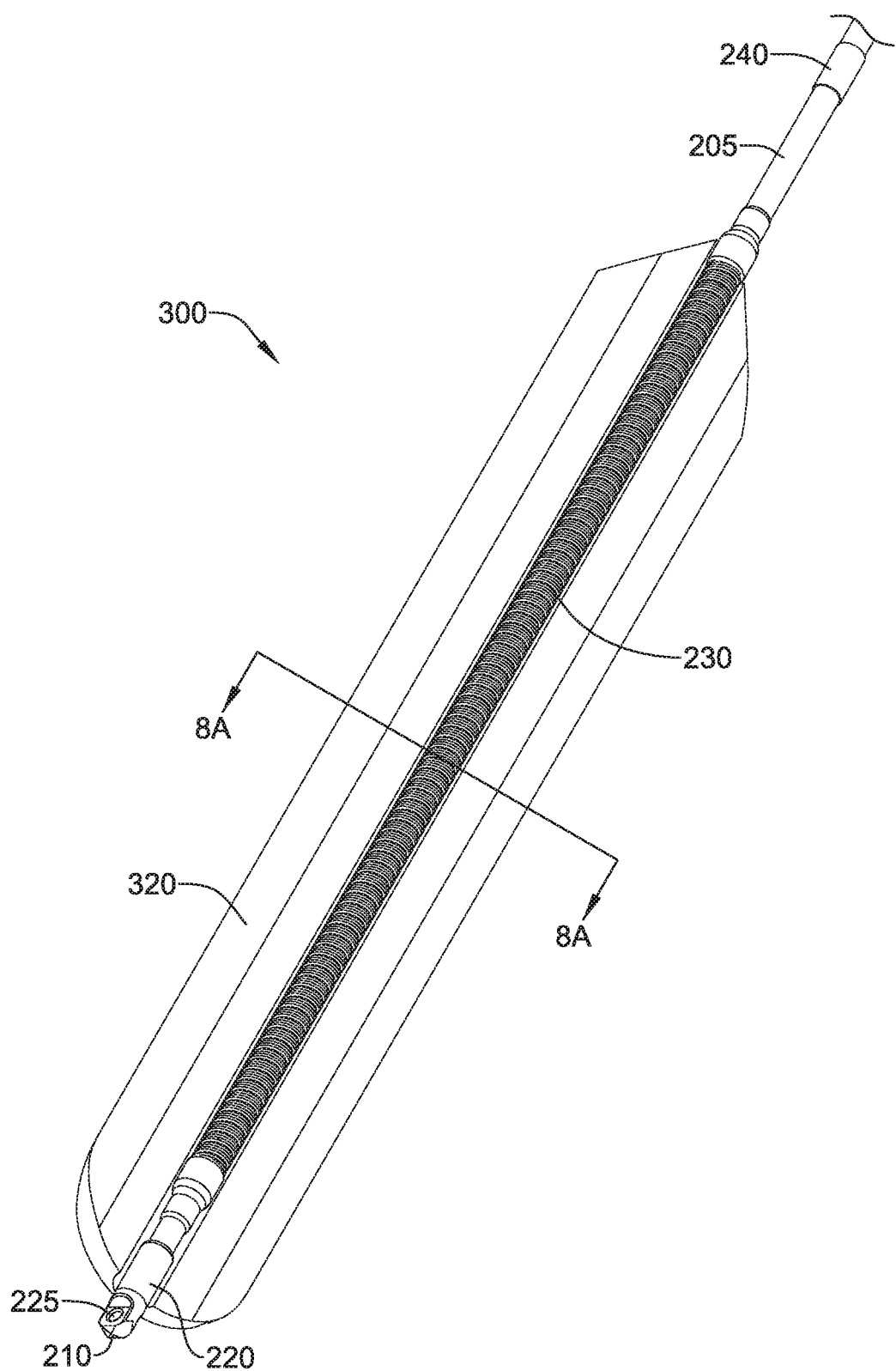
FIG. 7 shows an illustrative electrode for use with an implantable cardiac rhythm management system.

FIG. 7 shows a perspective view of an illustrative lead and electrode assembly 300 for use with an implantable cardiac rhythm management system, such as, but not limited to the S-ICD System™ from Cameron Health, Inc., and Boston Scientific Corporation described above with respect to FIG. 1. The lead and electrode assembly 300 may include the lead body 205, one or more electrodes 240, 230, 220, and a shield 320. The lead body 205 may include a proximal end (not shown) with a proximal pin which along with additional contacts serves in this example as an electrical contact, which may be separated by insulating material. The proximal end may further include seal plugs.

Figure 8A:
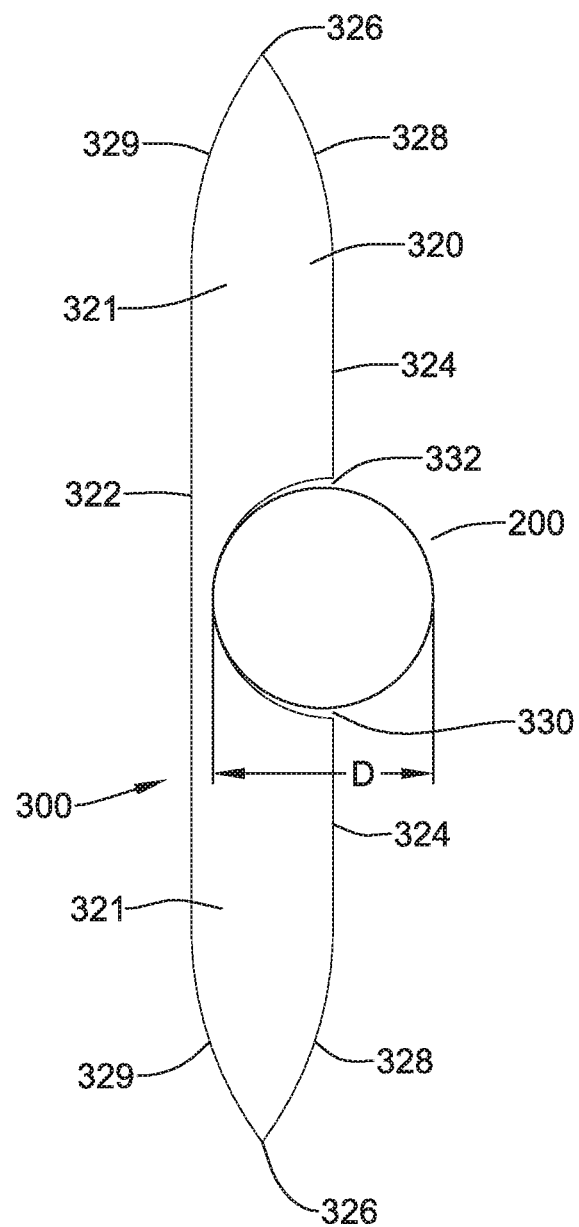
FIG. 8A shows a cross-sectional view of the electrode of FIG. 7, taken along line 8A-8A.

The shield 320 may be attached to the lead 200 forming an electrode assembly 300. The shield 320 may be attached such that it covers a first side of the coil electrode 230, as shown in FIGS. 7 and 8A. The shield 320 may be attached to the lead body 205 by adhesive, including any conventional medical adhesive. The shield 320 may be a molded single piece element, and may be molded in place over the lead body 205. Alternatively, the shield 320 may be formed in two or more pieces that are attached to the lead body 205. The shield 320 may be made of flexible materials such as silicone, rubber, plastics, or polymers such as polyurethane or polytetrafluoroethylene (PTFE), or composites thereof. In other examples, the shield 320 may be made of ceramic, and may have segments joined together to provide flexibility.

In some examples, the shield 320 may be visibly opaque or radiopaque to aid in orientation. In other examples, the shield 320 may be transparent. The shield may include one or more markers that may be visible to the naked eye or may be radiopaque. The markers may be located on the top surface 322 or the bottom surface 324, or both. The upper and lower surfaces of the shield 320 may be substantially flat, or may be angled relative to a transverse axis of the shield 320.

The shield 320 may extend over the shocking coil electrode 230, directing the shocking electrical energy in a direction away from the shield 320, towards the heart. In some examples, the shield 320 may extend longitudinally from the distal end 210 of the lead body 205 to a position proximate the proximal electrode 240. In the example shown in FIG. 7, the shield 320 extends from the distal electrode 220 to a position distal of the proximal electrode 240. In other examples, the shield 320 may extend over the proximal electrode 240.

The shield 320 may extend longitudinally beyond the coil electrode 230 in one or both the distal and proximal directions. In examples including a suture hole 225 or other attachment element at the distal end of the lead body 205, the shield 320 may extend from a position immediately proximal of the suture hole 225 or other attachment element to a position adjacent the proximal electrode 240. In other examples, the shield 320 may extend over only the coil electrode 320, or only a portion of the coil electrode 230. The shield may include a mating feature to secure with a suture hole on the distal end of a lead, or may include an opening that allows a suture passing through the suture hole of the lead to also pass through the suture hole in the shield.

FIG. 8A is a cross-sectional view of the device shown in FIG. 7, taken along line 8A-8A. In the example shown in FIG. 8A, the shield 320 has a top surface 322, a bottom surface 324, two top curved end regions 329 and two bottom curved end regions 328. The top and bottom curved end regions 329, 328 of each wing 321 meet at side points 326. The bottom surface 324 includes a groove, channel, or cavity 330 extending longitudinally along the length of the shield 320. The cavity 330 may be centrally located at the junction of first and second lateral sides or wings 321 that extend laterally beyond the lead 200. The wings 321 may extend laterally beyond the lead a distance equal to or greater than the diameter D of the lead 200. In some examples, the wings 321 may extend laterally beyond the lead 200 a distance of 1 to 3 times the diameter of the lead 200. The cavity 330 is sized and shaped to receive a portion of the lead 200.

As seen in FIG. 7, the length of the shield 320 extends along the longitudinal axis X-X of the lead 200. In the example shown in FIG. 8A, the cavity 330 extends circumferentially around approximately half of the lead 200. In other examples, the cavity 330 may extend circumferentially over less than half, such as one third, or more than half such as two thirds of the lead 200. In some examples, the cavity 330 may receive the lead 200 in a close fit, with the surface of the cavity 330 in contact with the lead along the entire cavity. In other examples, the diameter of the cavity 330 may be larger than the diameter of the lead 200 such that there is a space or gap 332 between the outer surface of the lead 200 and the cavity wall, as shown in FIG. 8A. The gap 332 may aid the shield wings 321 in flexing or bending towards the lead 200 during delivery. In some embodiments, the gap 332 may be closed when the lead 200 is attached to the shield 320, by bending the wings 321 into contact with the lead 200 after adhesive is applied between the lead and shield cavity. Once the adhesive is cured, the wings 321 may be bent slightly toward the lead 200, with the lead 200 in contact with the entire surface of the cavity, without any gap.

Figure 8B:
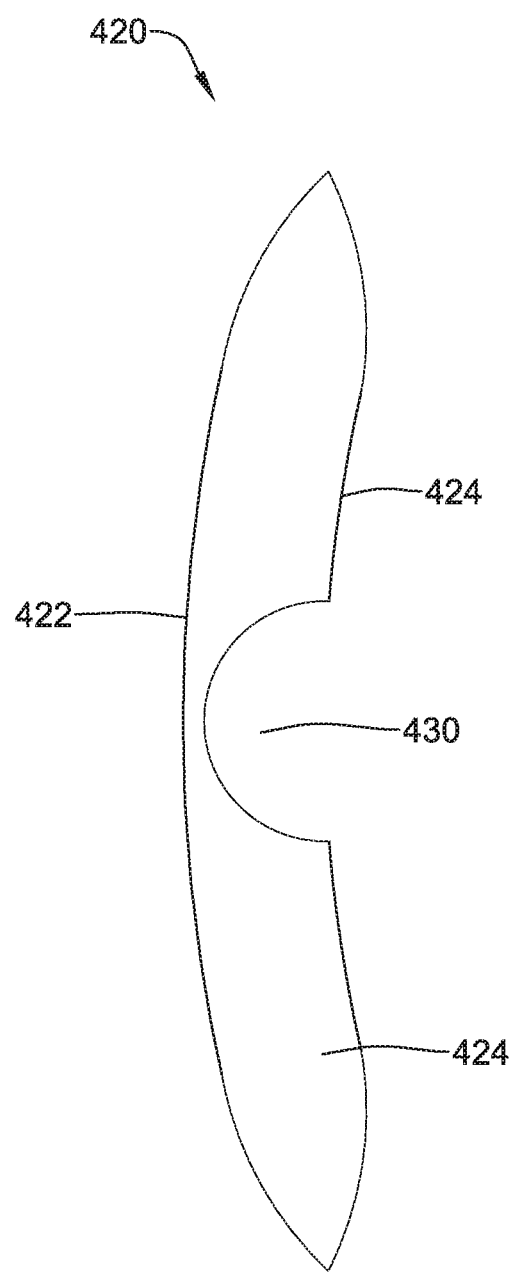
FIGS. 8B and 8C show cross-sectional views of other illustrative electrodes for use with an implantable cardiac rhythm management system.
Figure 8C:
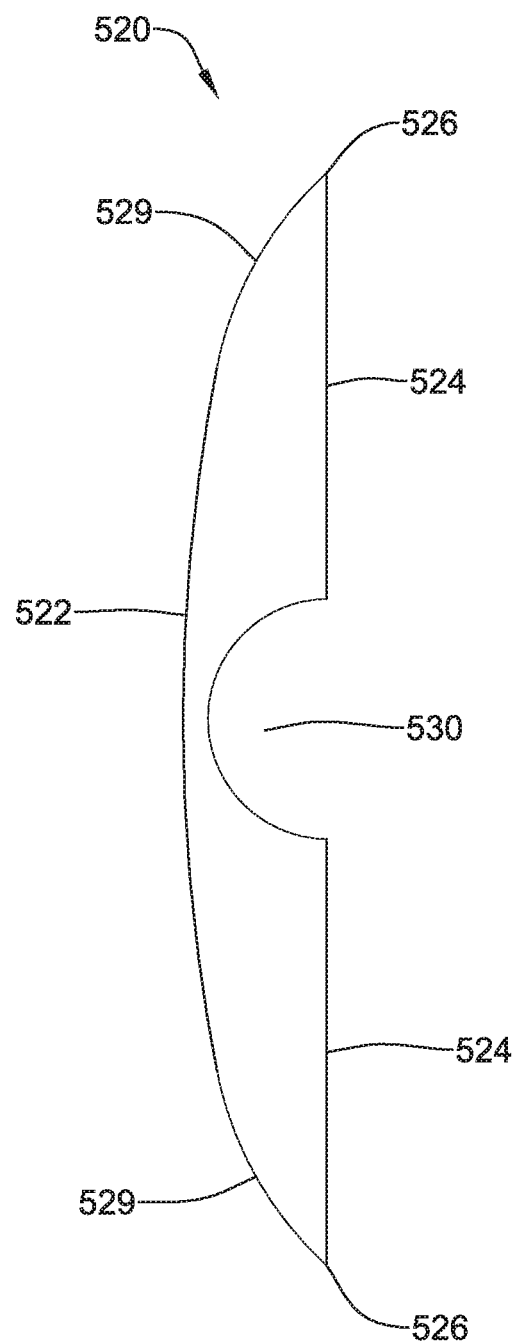

The shield 320 may have a generally flat top surface 322, as shown in FIG. 8A. In other examples, the top surface may be curved toward the lead 200, as shown in FIGS. 8B and 8C. The bottom surface 424 of the shield 420 may be curved to match the curve of the top surface 422, such that the bottom surface 424 and top surface 422 are parallel, as shown in FIG. 8B. The cavity 430 remains the same as that described for FIG. 8A. In other examples, the angles of curve for the top surface 422 and the bottom surface 424 may be different. The angle of curve for the bottom surface 424 may be larger or smaller than the angle of curve for the top surface 422. In other examples, such as that shown in FIG. 8C, the bottom surface 524 of the shield 520 may be generally flat with a cavity 530 disposed centrally within the bottom surface 524, while the top surface 522 is curved. The curve of the top surface 522 may be different from the curve of the curved end regions 529, as shown in FIG. 8C. In other examples, the curve of the top surface 522 may be a continuous curve between the two side points 526.

A thin permeable membrane may be positioned over the coil electrode 230 and/or other portions of the lead 200 not covered by the shield 320, to inhibit tissue ingrowth. Coatings, such as, but not limited to expanded polytetrafluoroethylene (ePTFE) may also be applied to the lead and electrode assembly 300, or portions thereof, to facilitate extraction and/or to reduce tissue ingrowth. In some embodiments, one or more of the electrodes 240, 230, 220 may include a high capacitive coating such as, but not limited to iridium oxide (IrOx), titanium nitride (TiN), or other "fractal" coatings which may be used, for example, to improve electrical performance. The lead and electrode assembly 300, or portions thereof, may include treatments in local areas to increase attachment to tissue and/or to increase effective surface area to yield reduced tissue interface impedance. For example, treatments may be applied along the length of the lead, near an electrode, or at or near the distal tip, the inclusion of a roughened surface, a surface of different polymer or other material, or a local a coating to encourage tissue growth such as a steroid.

Figure 9:
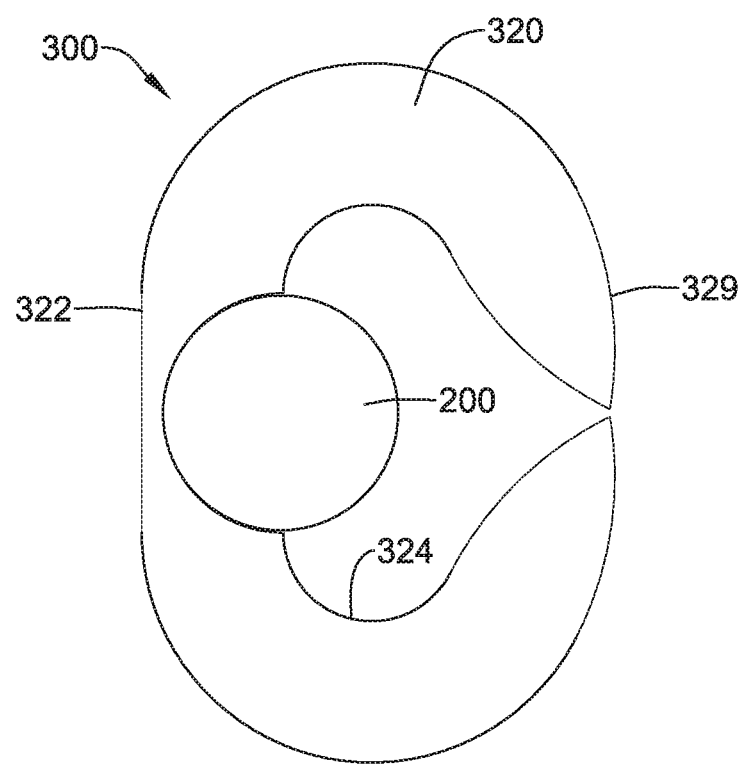
FIG. 9 shows a cross-sectional view of an electrode folded into a delivery configuration.

In some embodiments, the illustrated assembly 300 may be configured to move between a collapsed or delivery configuration, shown in FIG. 9, and an expanded or implanted configuration, shown in FIGS. 7 and 8A. However, it is contemplated that the illustrative lead and electrode assembly 300 of FIGS. 7 and 8A may be both the delivery configuration and the implanted configuration. The shield 320 may be flexible, allowing the wings to fold over the lead 200, as shown in FIG. 9. The folded assembly 300 may be delivered through a sheath to the desired subcutaneous location. Upon withdrawal of the sheath, the shield 320 may unfold into the implanted configuration, shown in FIG. 8A. For example, the wings may be made of an elastic or semi-resilient material to move between collapsed and expanded configurations, or a support structure in the wings may be provided using a shape memory metal such as Nitinol, to allow for a collapsed configuration to be created outside the body by a physician simply folding or crimping the wings down (or by pre-loading in a sheath) and, after implantation, the wings elastically move from the collapsed configuration to the expanded configuration.

An illustrative method of implanting the electrode assembly 300 may include the following steps. The patient may be prepared by delivery of anesthetics and or other medications and sterile field, etc. are prepared, as is known in the art. One or more incisions are then made, such as, for example, an incision in the left axilla and another at or near the xiphoid process. Some procedures may include one or more parasternal incisions for access to and implantation within one or both of the internal thoracic vein (ITV), as in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

Some procedures may further include a superior incision at or inferior to the manubrium for a subcutaneous implant procedure. Methods and devices for subcutaneous implantation of a lateral/axillary canister with parasternal lead are discussed further in U.S. Pat. No. 8,157,813, titled APPARATUS AND METHOD FOR SUBCUTANEOUS ELECTRODE INSERTION, and US PG Patent Publication No. 20120029335, titled SUBCUTANEOUS LEADS AND METHODS OF IMPLANT AND EXPLANT, the disclosures of which are incorporated herein by reference.

Alternatively, a substernal implant procedure may include a xiphoid or sub-xiphoid incision allowing tunneling along the back side of the sternum, such as in US PG Patent Publication No 20170021159, titled SUBSTERNAL PLACEMENT OF A PACING OR DEFIBRILLATING ELECTRODE, the disclosure of which is incorporated herein by reference. It has also been proposed to use a single-incision implant procedure with a steerable insertion tool, for example in US PG Patent Publication No. 20170020551, titled MINIMALLY INVASIVE METHOD TO IMPLANT A SUBCUTANEOUS ELECTRODE, or U.S. Pat. No. 6,647,292, titled UNITARY SUBCUTANEOUS ONLY IMPLANTABLE CARDIOVERTER-DEFIBRILLATOR AND OPTIONAL PACER the disclosures of which are incorporated herein by reference. If a subcutaneous implant position other than that shown in FIG. 1 is desired, the incisions may be placed elsewhere as desired, including for example, for use with right sided, anterior-posterior, or other implant positions such as shown in U.S. Pat. No. 6,721,597, titled SUBCUTANEOUS ONLY IMPLANTABLE CARDIOVERTER DEFIBRILLATOR AND OPTIONAL PACER, and U.S. Pat. No. 7,149,575, titled SUBCUTANEOUS CARDIAC STIMULATOR DEVICE HAVING AN ANTERIORLY POSITIONED ELECTRODE, the disclosures of which are incorporated herein by reference.

A subcutaneous or substernal tunnel for emplacement of a lead is then formed, for the most part, by separating tissue layers, as opposed to tearing through tissue layers themselves, and is desirably made as close to the fascia as possible in order to avoid capturing subcutaneous fat or other tissue in the electrical therapy field. Tunneling may be performed using a blunt-ended (for example, bullet-shaped) and stiff electrode insertion tool specially made for the purpose of tunneling to implant a subcutaneous electrode.

With the tunnel formed, a lead is emplaced. Various methods for emplacing the lead can be used. In some examples, a suture may be attached to an end of a lead after being passed through the subcutaneous tunnel and the suture is then used to pull the end of the lead from one incision to another (see, for example, US PG Patent Publication No. 20120029335 and or the labeling of the S-ICD System as originally approved by the FDA in PMA P11042). In other examples, tunneling may be performed with a splittable sheath placed over a tunneling tool, and the tunneling tool is removed while keeping the sheath in place, such that the lead can be inserted into the splittable sheath to the desired position. The shield 320 may be folded as shown in FIG. 9, prior to or as the lead is inserted into the sheath. Lead placement may also include securing the lead in a desired position by the use of sutures, clips, suture sleeves, or other devices and steps. For example, a suture sleeve integrated into or on the lead or a suture hole, as shown in FIG. 2, may be secured at a desired location such as (assuming implant as in FIG. 1) at the end of the lead along the sternum or near the xiphoid, with the suture being secured desirable to the fascia for secure anchoring. US PG Patent Publication No. 20170021159 also includes some discussion of anchoring for a substernal location.

Thus, as just described, the lead and shield implantation may be performed by inserting through an already placed sheath, or may be performed by placing a sheath over the lead and shield together and then implanting the sheath, lead and shield in one step. Either way, the sheath can be used to aid in securing or maintaining a collapsed configuration as shown in FIG. 9 for the wings during implantation. Removal of the sheath allows the elastic nature of the wings to cause the shield to assume the expanded configuration shown in other figures rather than the collapsed configuration of FIG. 9.

A pocket for receiving the canister of the device is also prepared. Pocket preparation may be done manually or using a blunt tool, for example. The ICD canister is then placed in the prepared pocket, and the lead is attached to the ICD canister. The exact order of steps may vary; in some examples, the lead is attached to the canister prior to placement of the canister. The ICD canister may be sutured to the fascia, if desired.

The system then may undergo configuration and testing as desired. Configuration may include setting various parameters, such as parameters for determining whether a treatable arrhythmia is occurring (for example, setting rate boundaries to define ventricular fibrillation and ventricular tachyarrhythmia for the patient), setting sensing parameters such as sensing vector selection, gain setting or other parameters, setting therapy parameters including pacing and defibrillation therapy parameters, or any other suitable parameters. System test may include the performance of induction testing, in which the patient's heart is placed in an arrhythmic state (such by inducing ventricular fibrillation by application of a stimulus on the T-wave, a long DC signal, or the use of a relatively fast 40 to 80 Hz signal), and the device is allowed detect the arrhythmia and deliver therapy to ensure both that the device can sense appropriately and that the delivered therapy will work for its intended purposes.

If system configuration and testing is completed appropriately, the procedure can end by closing all incisions and/or other appropriate post-surgery steps. As noted above, the steps may be performed in an order other than that described. Following the close of surgery, other testing and configuration steps may be performed as well prior to release of the patient, such as further setting of the sensing configuration, if desired.

Non-limiting examples include the following.

In a first example, an implantable device system may comprise an electrical lead having one or more electrodes thereon, and a shield attached to the electrical lead, the shield covering a first side of at least one of the one or more electrodes and extending laterally away therefrom the electrode, the shield directing energy from the at least one of the one or more electrodes in a direction away from the shield.

Alternatively or additionally to the example above, in a second example, the shield may have a top surface and a bottom surface, the top and bottom surfaces meeting at first and second side points at first and second lateral sides or wings of the shield, the bottom surface having a cavity therein, wherein the electrical lead is disposed within the cavity.

Alternatively or additionally to any of the examples above, in a third example, the one or more electrodes may include a shocking electrode, wherein the shield extends over the shocking electrode.

Alternatively or additionally to the example above, in a fourth example, the shocking electrode may be a coil electrode.

Alternatively or additionally to the example above, in a fifth example, the one or more electrodes may include one or more sensing electrodes, wherein the shield extends over at least one of the one or more sensing electrodes.

Alternatively or additionally to any of the examples above, in a sixth example, the top and bottom surfaces of the shield may be spaced apart creating an open space therebetween.

Alternatively or additionally to any of the examples above, in a seventh example, the entire shield may be a solid element.

Alternatively or additionally to any of the examples above, in an eighth example, the top and bottom surfaces may be parallel.

Alternatively or additionally to any of the examples above, in a ninth example, the top and bottom surfaces may be flat.

Alternatively or additionally to any of the examples above, in a tenth example, the top and bottom surfaces may be curved.

Alternatively or additionally to any of the examples above, in an eleventh example, the top surface may include first and second top curved end regions at first and second wings of the shield, and the bottom surface may include first and second bottom curved end regions at the first and second wings of the shield, wherein the first and second top curved end regions may join the first and second bottom curved end regions at the side points.

Alternatively or additionally to the example above, in a twelvth example, the top and bottom surfaces may be curved toward the lead.

Alternatively or additionally to any of the examples above, in a thirteenth example, the top surface may be curved and the bottom surface may be flat.

Alternatively or additionally to the example above, in a fourteenth example, the top surface may have a concave curve relative to the bottom surface.

Alternatively or additionally to the example above, in a fifteenth example, an angle of the concave curve of the top surface may be the same as an angle of the first and second top curved end regions, defining a single curve extending from the first side point to the second side point.

Alternatively or additionally to the example above, in a sixteenth example, the angle of the concave curve of the top surface may be different from the curve of the first and second top curved end regions.

Alternatively or additionally to any of the examples above, in a seventeenth example, the electrical lead may be attached to the shield with an adhesive.

Alternatively or additionally to any of the examples above, in an eighteenth example, the shield may be molded over the electrical lead.

Alternatively or additionally to any of the examples above, in a nineteenth example, a diameter of the electrical lead may be smaller than a diameter of the cavity, leaving a space on one or both sides of the electrical lead between an outer surface of the electrical lead and a surface of the cavity.

Alternatively or additionally to the example above, in a twentieth example, the shield may be flexible, wherein first and second laterally extending sides or wings of the shield may be moveable towards the electrical lead.

Alternatively or additionally to the example above, in a twenth-first example, the first and second wings may be configured to move towards the electrical lead, such that the outer surface of the electrical lead contacts the surface of the cavity, removing the space.

Alternatively or additionally to any of the examples above, in a twenty-second example, the shield may be flexible.

Alternatively or additionally to the example above, in a twenty-third example, the first and second wings may be configured to bend toward each other over the electrical lead.

Alternatively or additionally to any of the examples above, in a twenty-fourth example, a length of the shield may be at least twice a width of the shield.

Alternatively or additionally to the example above, in a twenty-fifth example, the length of the shield may be at least three times the width of the shield.

In a twenty-sixth example, a method of implanting an electrical lead may comprise making an incision in a patient, and inserting the implantable device system as in any of the first to twenty-fifth examples into the incision.

Alternatively or additionally to the example above, in a twenty-seventh example, inserting the implantable device system may include implanting the implantable device system with the shield facing the patient's skin and the electrical lead facing the patient's heart.

Alternatively or additionally to the example above, in a twenty-eighth example, the method may comprise, after making the incision in the patient, tunneling from the incision to a desired location, thereby creating a pathway, and then inserting the implantable device system along the pathway to the desired location.

Alternatively or additionally to the example above, in a twenty-ninth example, the method may comprise making a parasternal incision followed by accessing the internal thoracic vein (ITV), wherein inserting the implantable device system includes inserting the implantable device system into the ITV.

Alternatively or additionally to the example above, in a thirtieth example, the shield may comprise a flexible shield, wherein the method may comprise folding the shield, inserting the implantable device system to the desired location, and then unfolding the shield.

A thirty-first non-limiting example takes the form of a shield for use with an implantable lead for an active implantable medical device, the shield comprising a body having a length, a width, and a thickness, with a cavity extending into the thickness thereof along the length thereof for receiving the implantable lead, the shield adapted and configured to prevent current flow therethrough and direct electric current directed through the lead in a preferential direction.

Alternatively or additionally to the thirty-first example, in a thirty-second non-limiting example, the shield may further comprise a conductive portion in the cavity and extending along the cavity to redirect current from the lead in the preferential direction.

Alternatively or additionally to the thirty-first example, in a thirty-third non-limiting example, the body may be formed of a non-conductive material to prevent current flow therethrough.

A thirty-fourth non-limiting example takes the form of an implantable lead system comprising a shield as in any of the thirty-first to thirty-third examples and a lead having an electrode thereon, wherein the electrode is sized and shape to fit within the cavity of the shield.

Additionally or alternatively to the thirty-fourth non-limiting example, the lead may comprise a coil electrode and the shield may be of a length to hold and cover the coil electrode in the cavity.

Each of the above non-limiting examples can stand on its own, or can be combined in various permutations or combinations with one or more of the other examples.

The materials that can be used for the various components of the lead and electrode assembly, delivery tools, and/or other devices disclosed herein may include those commonly associated with medical devices. For simplicity purposes, the following discussion makes reference to accessory devices and their related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Other radiopaque marker bands and/or coils may also be incorporated into the design of the accessory devices and their related components to achieve the same result.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The Abstract is provided to comply with 37 C.F.R. § 1.72(b), to allow the reader to quickly ascertain the nature of the disclosure. It is submitted with the understanding that it will not be used to interpret or limit the scope or meaning of the claims.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable device system comprising:
   an electrical lead having one or more electrodes thereon including a lead body having a coil electrode with a diameter in the range of 1-5 mm placed over or formed on the lead body, the coil also having a coil length; and
   a shield for use with the electrical lead and comprising a body having a first end, a second end, and a length extending longitudinally therebetween, a width, and a thickness, wherein the length is greater than the width and extends from the first end to the second end, the shield body defining a cavity extending into the thickness and extending longitudinally along an entirety of the length of the shield,
   wherein the cavity is a channel that is open on one side along its entire length and is sized and shaped to receive the electrical lead with portions of the lead body extending longitudinally beyond the first and second ends of the shield, the shield further comprising first and second wings extending radially away from a longitudinal axis of the shield on either side of the cavity, the shield adapted and configured to prevent current flow therethrough and direct electric current output through the electrical lead in a preferential direction through the open side of the channel;
   wherein when the electrical lead is disposed in the cavity of the shield, the cavity extends circumferentially around at least one third of a circumference of the lead.

2. The implantable device system of claim 1, wherein the shield further comprises a conductive metal portion in the cavity and extending along the cavity to redirect current from the lead in the preferential direction.

3. The implantable device system of claim 1, wherein the shield body is formed of a non-conductive material to prevent current flow therthrough.

4. The implantable device system of claim 1, wherein the wings are configured to collapse toward each other over the cavity for purposes of implantation, defining thereby a collapsed configuration for implantation and an expanded configuration for use.

5. The implantable device system of claim 4 wherein the wings are elastic such that the shield can be implanted into a patient in the collapsed configuration and then the elasticity of the wings causes the wings to expand to the expanded configuration.

6. The implantable device system of claim 5, wherein the shield further comprises a shape memory metal support structure adapted to add to the elasticity of the wings.

7. The implantable device system of claim 5 wherein the wings are elastic and require a sheath thereon for purposes of implantation.

8. The implantable device system of claim 1, wherein the length of the shield is at least twice the width of the shield.

9. The implantable device system of claim 1, wherein the entire shield is a solid element.

10. The system of claim 1, wherein the electrical lead is attached to the shield with an adhesive such that the entire coil is disposed within the cavity.

11. The system of claim 1 further comprising an implantable pulse generator adapted to use the coil electrode over which the shield is placed for delivery of defibrillation therapy.

12. A method of treating a patient by implanting a cardiac defibrillation lead and a shield, the lead having thereon a coil electrode with a diameter in the range of 1-5 mm, and the shield having a first and a second end defining a length therebetween, the shield also having a width less than the length and defining a cavity extending longitudinally along an entirety of the length of the shield, the cavity being a channel having a first open side, the channel sized and shaped to receive a portion of the lead including the defibrillation coil, the method comprising:
  making an incision in a patient;
  inserting a sheath containing the lead and shield through the incision to a desired position in the patient to thereby implant the lead and shield at the desired position in the patient, wherein:
    the shield further includes first and second wings extending radially away from either side of the cavity, the first and second wings being flexible to allow for an expanded configuration in which the wings extend in opposing directions relative to the cavity and a collapsed configuration in which the wings wrap over the cavity and toward one another, and
    the inserting step is performed with the lead disposed within the cavity of the shield and with the wings constrained in the collapsed configuration by the sheath; and
  removing the sheath thereby allowing the wings to return to the expanded configuration.

13. The method of claim 12, wherein the shield has a first side on which the cavity extends and a second side opposite the first side, and the step of inserting the lead and shield is performed such that the first side faces the patient's heart.

14. The method of claim 12 wherein the step of inserting the lead and shield through the incision comprises inserting the lead and shield into a substernal position in the mediastinum.

15. The method of claim 12 wherein the step of inserting the lead and shield through the incision comprises inserting the lead and shield to a subcutaneous position.

16. The method of claim 12, wherein the shield includes a conductive metal layer extending along the cavity to redirect current from the coil electrode in a preferential direction.

17. A subcutaneous implantable defibrillator comprising:
  an implantable pulse generator having a port;
  an implantable subcutaneous lead having a plurality of electrodes thereon including a lead body having at least a coil electrode formed or placed on the lead body, the coil electrode having an outer diameter in the range of 1-5 mm, the lead being adapted to couple with the port; and
  a shield having a first end, a second end, and a length extending longitudinally therebetween, the shield having a first side with a channel extending longitudinally along an entirety of the length of the shield, the channel being open along an entirety of its length and sized and shaped for receiving the lead with portions of the lead extending longitudinally beyond the first and second ends of the shield, the shield having a second side, and wings extending radially away from a longitudinal axis of the shield on either side of the channel, the shield adapted to direct energy from a selected one or more of the electrodes of the implantable subcutaneous lead in a preferred direction toward the heart of a patient.

18. The subcutaneous implantable defibrillator of claim 17, wherein the shield includes a conductive metal layer extending along the cavity to redirect current from the coil electrode in the preferential direction.

* * * * *